(12) United States Patent
Goldberg et al.

(10) Patent No.: US 11,139,079 B2
(45) Date of Patent: Oct. 5, 2021

(54) COGNITIVE STROKE DETECTION AND NOTIFICATION

(71) Applicant: INTERNATIONAL BUSINESS MACHINES CORPORATION, Armonk, NY (US)

(72) Inventors: Itzhack Goldberg, Hadera (IL); Raquel Norel, Yorktown Heights, NY (US); Kahn Rhrissorrakrai, Woodside, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 930 days.

(21) Appl. No.: 15/450,603

(22) Filed: Mar. 6, 2017

(65) Prior Publication Data

US 2018/0253530 A1    Sep. 6, 2018

(51) Int. Cl.
*G16H 50/20* (2018.01)
*A61B 5/00* (2006.01)
(Continued)

(52) U.S. Cl.
CPC .......... *G16H 50/20* (2018.01); *A61B 5/0077* (2013.01); *A61B 5/4803* (2013.01); *G16H 40/67* (2018.01); *G16H 50/50* (2018.01)

(58) Field of Classification Search
CPC ... A61B 5/4058; A61B 5/4064; A61B 5/6898; A61B 5/7282; A61B 5/74; A61B 5/112;
(Continued)

(56) References Cited

U.S. PATENT DOCUMENTS 7,115,103 B2   10/2006   Keith et al.
7,558,622 B2    7/2009   Tran
(Continued)

FOREIGN PATENT DOCUMENTS

CN   101976450 A     2/2011
EP     1509042 A1    2/2005
WO  2006109268 A1   10/2006

OTHER PUBLICATIONS http://strokeassociation.org/STROKEORG/WarningSigns/Stroke-Warning-Signs-and-Symptoms_UCM_308528_SubHomePage.jsp); accessed online Aug. 24, 2016, five pages.
(Continued)

*Primary Examiner* — Paras D Shah
(74) *Attorney, Agent, or Firm* — Cantor Colburn LLP; Kristofer Haggerty

(57) ABSTRACT

Embodiments of the invention include methods, systems, and computer program products for determining stroke onset. Aspects of the invention include determining a baseline behavioral model for a user and receiving real-time user data from a personal portable device. Aspects of the invention also include analyzing the real-time user data to determine the presence of an abnormal event. Aspects of the invention also include, based at least in part on a determination that the abnormal event is present, conducting a plurality of stroke analyses to generate a plurality of impairment characteristics. Aspects of the invention also include integrating the plurality of impairment characteristics, comparing the integrated plurality of impairment characteristics to the baseline behavioral model and outputting a stroke onset determination.

19 Claims, 8 Drawing Sheets

(51) Int. Cl.
*G16H 50/50* (2018.01)
*G16H 40/67* (2018.01)

(58) Field of Classification Search
CPC ....... A61B 5/01; A61B 5/0077; A61B 5/0404; A61B 5/681; A61B 5/6803; A61B 5/6804; A61B 5/746; A61B 5/742; A61B 5/0022; A61B 5/2055; G10L 15/00; G10L 15/262; G10L 25/48; G10L 25/51; G10L 25/60
See application file for complete search history.

(56) References Cited

U.S. PATENT DOCUMENTS

| | | | |
|---|---|---|---|
| 8,241,221 B2 | 8/2012 | Park | |
| 2008/0001735 A1* | 1/2008 | Tran | A61B 5/0022 340/539.22 |
| 2008/0317297 A1 | 12/2008 | Willmann et al. | |
| 2009/0018407 A1* | 1/2009 | Jung | A61B 5/0022 600/301 |
| 2014/0016860 A1 | 1/2014 | Senechal et al. | |
| 2014/0276123 A1 | 9/2014 | Yang | |
| 2015/0005645 A1 | 1/2015 | Thompson | |
| 2016/0095518 A1 | 4/2016 | Convents et al. | |
| 2016/0213318 A1 | 7/2016 | Parodi et al. | |
| 2017/0007167 A1* | 1/2017 | Kostic | A61B 5/0077 |
| 2017/0195637 A1* | 7/2017 | Kusens | G06K 9/4604 |
| 2018/0317811 A1* | 11/2018 | Lee | A61B 5/1116 |

OTHER PUBLICATIONS http://www.strokeassociation.org/STROKEORG/AboutStroke/BLS/Treatment_UCM_310892_Article.sp#quicktreatment); accessed Online Aug. 24, 2016, five pages.
Leijdekkers et al, "A Self-Test to Detect a Heart Attack Using a Mobile Phone and Wearable Sensors," Faculty of IT, University of Technology Sydney, Broadway 2007 NSW Australia, six pages.
Norel, et al., "Cognitive System to Detect and Notify of Onset of Stroke," (http://www.strokeassociation.org/STROKEORG/AboutStroke/BLS/Treatment_UCM_310892_Article.jsp#quicktreatment), online—Nov. 4, 2016.

* cited by examiner

COGNITIVE STROKE DETECTION AND NOTIFICATION

BACKGROUND

The present invention relates in general to medical devices, and more specifically to methods, systems, and computer program products for a portable device that provides timely recognition and notification of stroke symptoms.

Approximately 800,000 people every year suffer from a stroke in the United States alone. Stroke is a leading cause of death and also the leading cause of serious long-term disability. If a stroke victim receives attention, particularly in a clinical setting, within three hours of the onset of attack, he or she has a significantly greater chance of recovering without suffering major ill effects. Thus, timely recognition of a stroke and fast medical attention can be imperative for desirable patient outcomes.

Some conventional methods for detection of stroke can rely upon a manual assessment by an individual or, in some cases, the performance of a self-assessment to identify several symptoms associated with stroke. However, ability to perform such assessments can easily be hindered by the symptoms experienced by the stroke victim and unpredictability of being in proximity to an individual capable of manually assessing the stroke victim.

Although automated methods of stroke detection that leverage only speech analysis have been proposed, for example to identify slurred or altered speech, such reliance upon speech can result in high levels of false positives. Moreover, individuals can desire to use a stroke onset detection system without the need for wearing cumbersome equipment.

A need remains for timely stroke onset detection with minimal false positives that can be performed in the absence of medical personnel.

SUMMARY

In accordance with one or more embodiments of the invention, a computer program product for determining stroke onset is provided. The computer program product includes a computer readable storage medium readable by a processing circuit and storing program instructions for execution by the processing circuit for performing a method. The method includes determining a baseline behavioral model for a user. The method also includes receiving real-time user data from a personal portable device. The method also includes analyzing the real-time user data to determine the presence of an abnormal event. The method also includes conducting a plurality of stroke analyses to generate a plurality of impairment characteristics based at least in part on a determination that the abnormal event is present. The method also includes integrating the plurality of impairment characteristics. The method also includes comparing the integrated plurality of impairment characteristics to the baseline behavioral model. The method also includes outputting a stroke onset determination. Advantageously, such computer program products can detect and assess the onset of a stroke without the need for multiple specialized devices or corroboration by another individual.

In accordance with a further embodiment, a computer-implemented method for determining stroke onset is provided. The method includes determining a baseline behavioral model for a user. The method also includes receiving real-time user data from a personal portable device. The method also includes analyzing the real-time user data to determine the presence of an abnormal event. The method also includes conducting a plurality of stroke analyses to generate a plurality of impairment characteristics based at least in part on a determination that the abnormal event is present. The method also includes integrating the plurality of impairment characteristics. The method also includes comparing the integrated plurality of impairment characteristics to the baseline behavioral model. The method also includes outputting a stroke onset determination. Desirably, such computer-implemented methods can detect and assess the onset of a stroke without the need for multiple specialized devices or corroboration by another individual.

In accordance with another embodiment, a processing system for determining stroke onset includes a processor in communication with one or more types of memory. The processor is configured to determine a baseline behavioral model for a user. The processor is also configured to receive real-time user data from a personal portable device. The processor is also configured to analyze the real-time user data to determine the presence of an abnormal event. The processor is also configured to conduct a plurality of stroke analyses to generate a plurality of impairment characteristics based at least in part on a determination that the abnormal event is present. The processor is also configured to integrate the plurality of impairment characteristics. The processor is also configured to compare the integrated plurality of impairment characteristics to the baseline behavioral model. The processor is also configured to output a stroke onset determination. Advantageously, such processing systems can detect and assess the onset of a stroke without the need for multiple specialized devices or corroboration by another individual.

BRIEF DESCRIPTION OF THE DRAWINGS

The subject matter of embodiments of the invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

Figure 1:
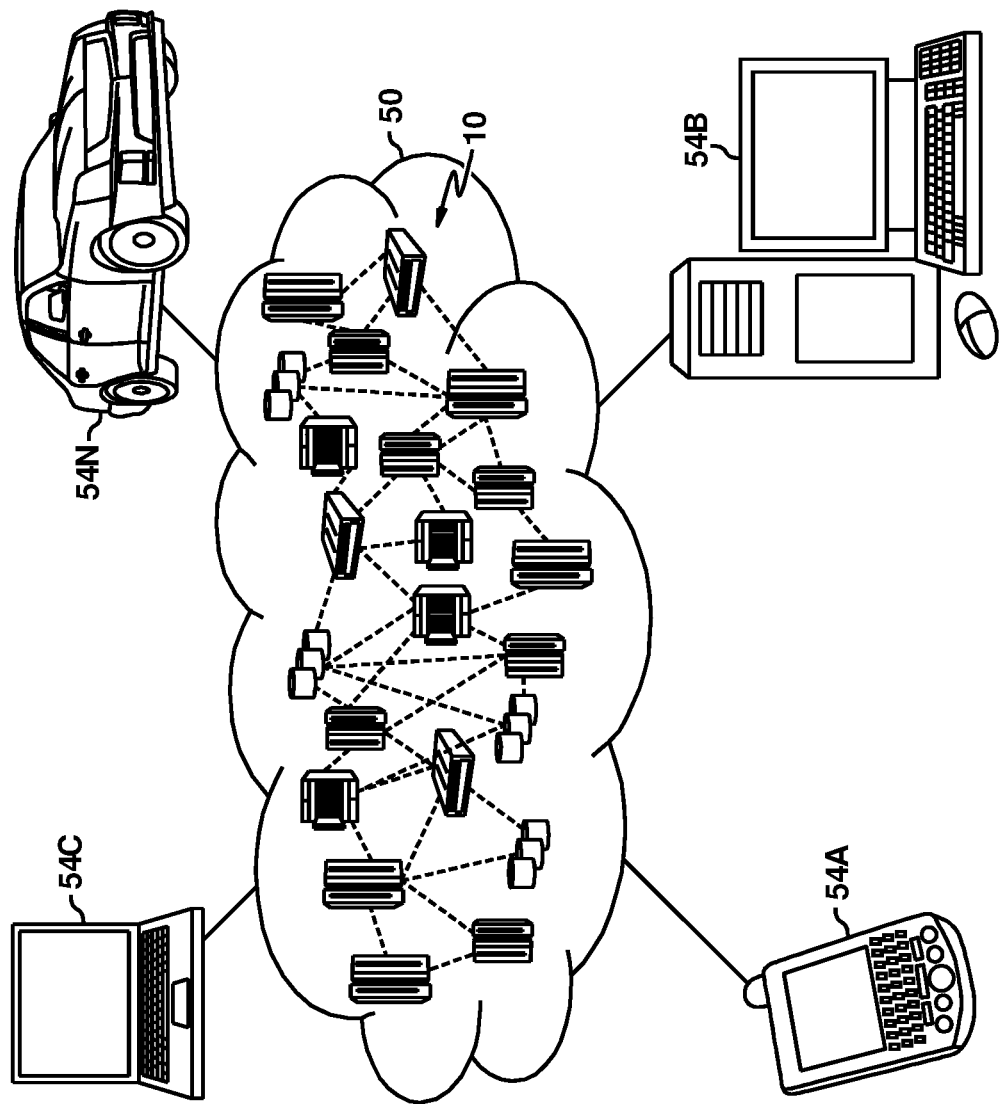
FIG. 1 depicts a cloud computing environment according to one or more embodiments of the present invention.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 is depicted according to one or more embodiments of the present invention. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
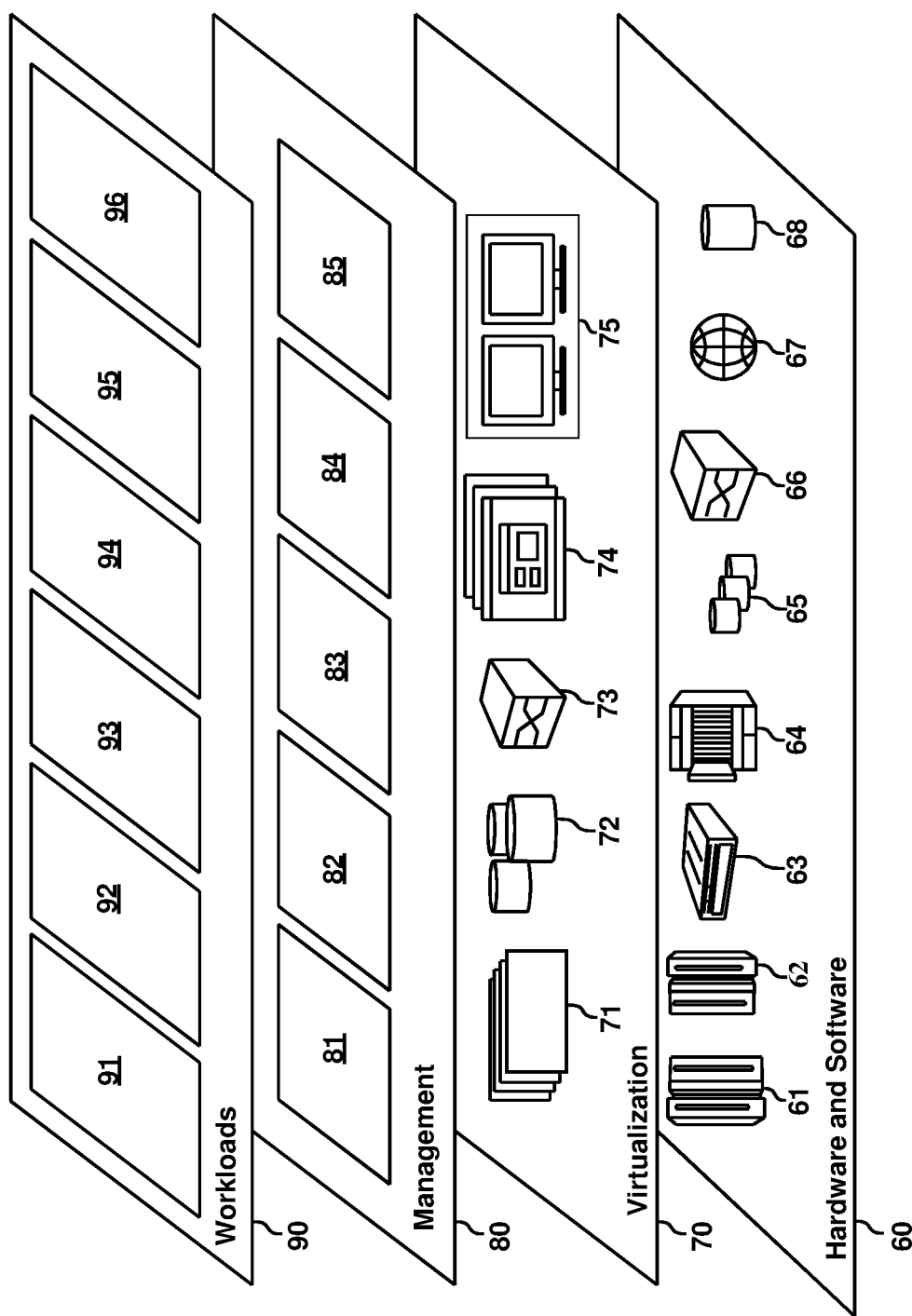
FIG. 2 depicts abstraction model layers according to one or more embodiments of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and detection and notification of stroke onset 96.

Figure 3:
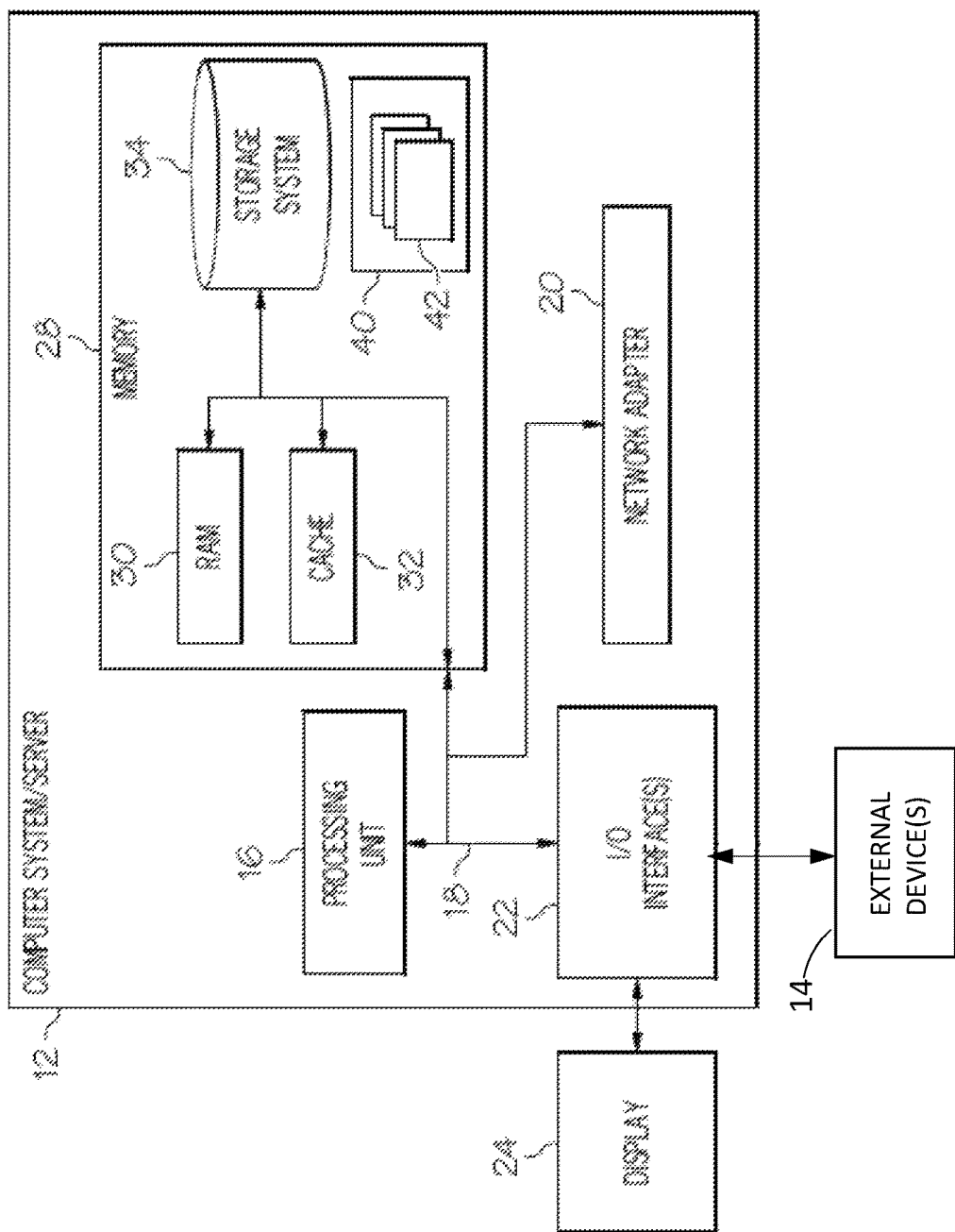
FIG. 3 depicts a computer system according to one or more embodiments of the present invention.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Timely recognition of a stroke and fast medical attention upon stroke onset can be imperative. Unlike a cardiac arrest, where there can be at most a four minute window to avoid irreversible injuries, including brain damage, the value of early stroke recognition is high. A stroke victim can have a grace period about three hours to receive treatment and, thereby, have a relatively high chance to be saved and recover without major ill effects.

Many existing methods for detection of stroke rely upon a manual assessment of an individual or reliance on an individual's self-assessment based upon prior education of stroke symptoms. Known symptoms of stroke that can be manually or individually assessed include (1) sudden numbness or weakness of the face, arm, or leg, particularly on one side of the body; (2) inability to maintain arms at a symmetric horizontal level; (3) slurred speech; (4) sudden trouble seeing from one or both eyes; (5) sudden trouble walking, dizziness, or loss of balance and coordination; and (6) sudden severe headache with no known cause. The ability to assess these symptoms, however, can be hindered by the onset of stroke itself or the proximity (or lack of proximity) to another individual with the awareness and knowledge needed to administer the assessment. For example, the acronym "F.A.S.T." can be used to help individuals self-assess their symptoms or the symptoms of others in connection with early stroke detection. The instructions and symptoms denoted by "F.A.S.T." include: Face drooping, which asks whether one side of the face droops or is numb; Arm weakness, which asks whether one arm is weak or numb and includes a request for an individual to raise both arms and to identify whether one arm drifts downward; Speech difficulty, which asks whether speech is slurred or if the person is unable to speak or hard to understand and requests that an individual repeat a simple sentence and the assessor determine whether the sentence was correctly recited; and Time to call 911, which requests a call to emergency personnel if anyone shows any of the aforementioned symptoms.

Turning now to an overview of aspects of the present invention, systems and methodologies for timely recognition of stroke symptoms using a portable personal device, such as a smart phone, are provided. Embodiments of the invention allow continuous or periodic monitoring of user actions and/or behavior for signs of stroke. In some embodiments of the invention, systems and methods perform a medical assessment to assess onset of stroke, including guided and/or automated assessments performed with a smart phone.

In today's era, many people carry a portable personal device that includes a sophisticated computing device, for instance a smart phone, which can be leveraged to provide a tool for the detection and early or even immediate notification of medical emergencies, such as a stroke. Embodiments of the present invention leverage cognitive computing techniques to integrate multiple vectors of information. In some embodiments, the invention provides an active, always-on, and highly personalized monitoring system for detecting and assessing signs of a stroke event. Upon detection of signs of a stroke event, embodiments of the invention provide a rapid assessment of stroke systems before notifying emergency medical services or designated emergency contacts. Embodiments of the invention include systems and methods that detect and assess the onset of stroke without the need for multiple specialized devices or corroboration by another individual.

Figure 4:
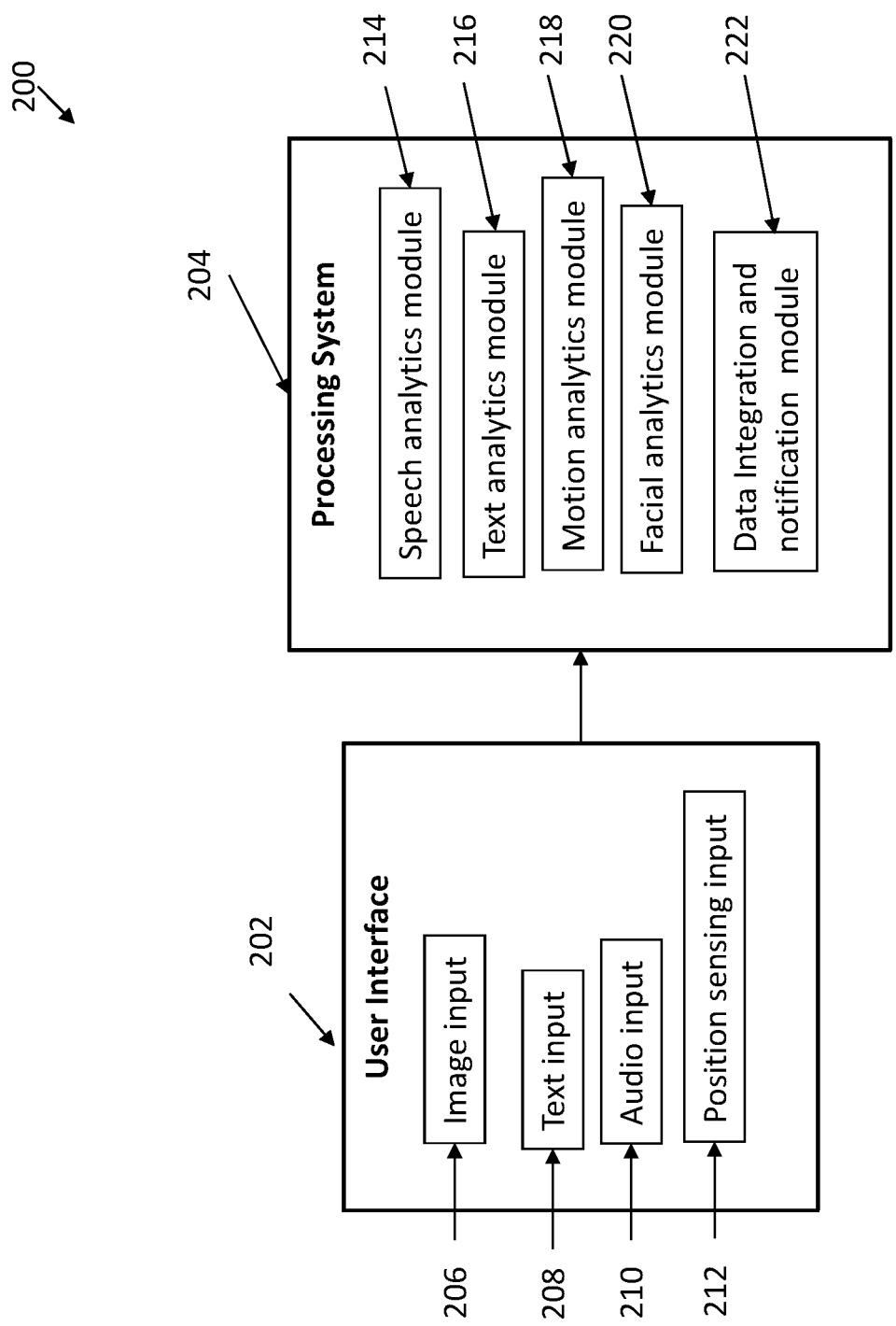
FIG. 4 is a block diagram illustrating a system for cognitive detection and notification of stroke onset according to one or more embodiments of the present invention.

Turning now to a more detailed description of one or more embodiments of the invention, FIG. 4 illustrates an exemplary system 200 for cognitive detection and notification of stroke onset according to one or more embodiments of the present invention. The system 200 can be included within a smartphone, cell phone, smart watch, or any other personal portable device. The system 200 includes a user interface 202 and a processing system 204.

The user interface 202 can include an image input 206, a text input 208, an audio input 210, such as a microphone system, and a position sensing input 212. The image input 206 can include a camera, such as a camera embedded within a smartphone or smartwatch. The text input 208 receives textual data from a user and can include a keyboard interface, for example, a keyboard or a virtual keyboard linked to a personal portable device, such as a computer simulated keyboard on a touch screen. The audio input 210 receives audio signals from a user and can include, for example, a microphone embedded within a smart device or a microphone on a device in wired or wireless communication with the smart device, such as a Bluetooth connected headset. The position sensing input 212 can include, for example, an accelerometer, a gyroscope, a global positioning system, and/or any other device capable of providing positional information and can include devices embedded within a smart device or devices external to and in communication with a smart device, such as wearable fitness sensors and activity trackers.

The processing system 204 includes a plurality of modules for analyzing and integrating user input. The modules can record and analyze data over a period of time, continuously, periodically, and/or in real-time. In some embodiments of the invention, the modules develop baseline or threshold models of behavior. In some embodiments of the invention, the threshold or baseline models of behavior can be personalized to a user. In some embodiments of the invention, the threshold or baseline models of behavior include data of other users. In some embodiments of the invention, the models are contextualized or correlated with a plurality of secondary factors, including temporal factors, such data reflecting the time of day, week, month, or year; age; gender; geographic location; active state; and the like. After a baseline behavioral model is established, embodiments of the invention monitor in real-time speech, text entry, and/or user position for significant deviations from the baseline behavioral model. Based upon the strength, number, and type of deviations detected over a given period of time, the system 200 can alert a user to a possibility of stroke and engage an automated assessment protocol before notifying emergency services.

In some embodiments of the invention, the processing system 204 includes a speech analytics module 214. The speech analytics module 214 can record and analyze user data over an initial period of time, such as in collection of a training data set, to develop a baseline behavioral speech model. In some embodiments of the invention, the baseline behavioral speech model is updated over time for further personalization to a user or population. The speech analytics module 214 can include baseline population data, including linguistic data for a plurality of users or for populations and population subsets. The speech analytics module 214 can receive and analyze the rate of translation of audible signals by a processor, the comprehensibility of words or sentences, the structure and sentiment of sentences, consistency of meaning or tone in speech, and can be further tailored to multilingual individuals, individuals having particular geographic or personal characteristics. The speech analytics module 214 analyzes verbal speech of a user, for example through telecommunication activities or by continuous monitoring in an always-listening mode. In some embodiments of the invention, speech analytics model 214 can receive audio input 210 from the user interface 202. Methods of speech detection and analytics are known.

In some embodiments of the invention, speech is assessed for comprehensibility. For example, to assess for comprehensibility, the speech analytics module 214 can employ known methods and systems, such as speech recognition systems integrated within cellular or smart devices, to aid in a determination of whether a user's speech is comprehensible. For example, a smart phone equipped with speech recognition applications can be integrated into the speech analytics module 214 and can determine whether or how the system can understand a user. If the system 200 cannot understand the user, the speech analytics module 214 can register an abnormal event.

In some embodiments of the invention, the speech analytics module 214 can assess the real-time rate at which the system 200 is able to confidently identify a corresponding dictionary word to the user's speech and can compare the real-time rate to a baseline rate. The speech analytics model can determine whether the real-time rate at which the dictionary word is matched to the user's speech significantly differs from the baseline rate. A significant difference can indicate difficulty speaking or verbal confusion and could be attributed to an abnormal event.

In some embodiments of the invention, speech analytics module 214 can perform a linguistic analysis on the structure and sentiment of a user's sentences and can compare real-time linguistic analysis results to a baseline linguistic analysis model. A baseline linguistic analysis model can include historical data from the user, data from the user collected as part of a training data set, and/or data representative of a larger population. For example, if structures or sentiments significantly differ from the user's norm or are determined to be inconsistent with population level patterns, the linguistic data can be attributed to an abnormal event.

In some embodiments of the invention, when the speech analytics module 214 detects an abnormal event or a significant deviation from the baseline behavioral model, the speech analytics module 214 can enter into an assessment mode. In assessment mode, the speech analytics module can perform one or more verbal evaluations to determine the presence and degree of speech impairment.

In some embodiments of the invention, the processing system 204 includes a text analytics module 216. The text analytics module analyzes text input 208 to detect and analyze indicators of stroke onset. The text analytics module 216 can record and analyze user data over an initial period of time, such as in collection of a training data set, to develop a baseline textual model. In some embodiments of the invention, the baseline textual model is updated over time for further personalization to a user or population. The text analytics module 216 can operate continuously, periodically, in real-time, or whenever text input 208 is received to the processing system 204. The text analytics module 216 can operate in a detection mode and in an assessment mode.

In detection mode, the text analytics module 216 can analyze text input whenever the keyboard system of a personal portable device, such as a smartphone, is active. In some embodiments of the invention, the text analytics module 216 analyzes comprehensibility. In some embodiments of the invention, the text analytics module 216 analyzes a typographical error rate. In some embodiments of the invention, the text analytics module 216 collects training data from a user, personalizing text input characteristics to a user. For example, a text analytics module 216 can calculate a personal text input profile for a user including one or more of a baseline text entry rate, typographical error rate, text correction rate, normative sentence structure, and normative sentiment of sentences and phrases. In some embodiments of the invention, the text analytics module 216 is trained for multilingual individuals. In some embodiments of the invention, the text analytics module 216 compares real-time text entry to a personal text input profile for a user. A significant text entry deviation in comparing real-time text entry to the personal text input profile can indicate an abnormal event.

In assessment mode, the text analytics module 216 can perform textual assessments for detection and characterization of stroke onset. In assessment mode, the speech analytics module can perform one or more textual evaluations to determine the presence and degree of impairment. For example, a text analytics module 216 can prompt a user to type a predetermined phrase or sentence with a keyboard of a smartphone. The text analytics module 216 can compare the phrase or sentence accuracy, the time of input, or other parameters to a personalized baseline prediction or to a calculated threshold. A significant deviation from the personalized baseline or a result exceeding the threshold can indicate impairment associated with stroke onset.

In some embodiments of the invention, the processing system 204 includes a motion analytics module 218. The motion analytics module 218 can operate continuously, periodically, in real-time, or whenever position sensing input 212 is available. In some embodiments of the invention, the motion analytics module 218 develops baseline or threshold models of behavior. In some embodiments of the invention, the threshold or baseline models of behavior can be personalized to a user. The motion analytics module can operate in a detection mode and in an assessment mode.

In detection mode, the motion analytics module analyzes user movement to detect and analyze indicators of stroke onset. The motion analytics module 218 can use position sensing input 212 to detect and analyze user movement, such as sitting, standing, walking, driving, running, and falling or laying down. In some embodiments of the invention, the motion analytics module 218 receives position sensing input 212 from a personal user device, such as a smartphone or smartwatch or external devices in communication with a smartphone or smartwatch. The motion analytics module 218 can develop personalized or generalized baseline movement thresholds and characteristics in a baseline movement model and can compare user movement, detected through position sensing input 212, to the baseline movement thresholds and characteristics to determine the presence of a confused or dizzy state. In some embodiments of the invention, movement patterns and characteristics of stroke victims are included within a baseline model. Baseline model can include, in some embodiments of the invention, walking routes common to a user, walking pace ranges for a user, and walking stride ranges for a user. For example, motion analytics module 218 can analyze walking characteristics, including gait, stride, pace, and/or path when a user is walking and can compare the results of the analysis to baseline movement thresholds and characteristics. A significant difference in route from a baseline model or a significant difference in pace can indicate impairment associated with stroke.

In assessment mode, the motion analytics module 218 can perform motion assessments for detection and characterization of stroke onset. For example, a motion analytics module 218 can prompt a user to raise their arms to a horizontal plane and can analyze the resultant user action with a smartphone camera system to determine if one or both arms are drooping. For example, a camera can be positioned near a user to record a user arm raising action via video. The motion analytics module 218 can detect the position of the arms of the user relative to the user body or to a horizontal plane and compare the degree of deviation from the horizontal plane to a baseline model or to a threshold value. Alternatively, a user can be instructed to hold a smartphone during the process of raising one or both arms while the smartphone camera is recording video of the surrounding area with the smartphone camera during the user motion. The motion analytics module 218 can calculate or estimate a degree of deviation from the horizontal plane based on the relative position of images of surrounding objects in the captured video. A significant degree of deviation from the horizontal plane after instruction to raise arms to the horizontal plane can indicate impairment associated with stroke onset.

In some embodiments of the invention, the processing system 204 includes a facial analytics module 220. The facial analytics module 220 can calculate a baseline facial model using historic image input or input collected as part of a training data set. The facial analytics module 220 can calculate a personalized baseline, for example, by calculating facial symmetry in images depicting the user's face performing one or more actions. For example, facial analytics module 220 can calculate symmetry profiles of a user performing the actions of smiling, frowning, raising eyebrows, or performing similar facial expressions. In operation, for instance, facial analytics module 220 can prompt a user to smile, collect an image of the user face from a smartphone camera, calculate the symmetry of the user face, and compare the symmetry of the user face to a personalized baseline or to a generalized threshold symmetry. A significant deviation from the personalized baseline or generalized threshold symmetry can indicate impairment associated with stroke onset.

In some embodiments of the invention, the processing system 204 includes a data integration and notification module 222. In some embodiments of the invention, the data integration and notification module 222 can record and analyze user data from a plurality of inputs, including image and video input, text input, audio input, and position sensing input, over an initial period of time, such as in collection of a training data set, to develop a baseline behavioral model. In some embodiments of the invention, data integration and notification module 222 can include baseline population data, including characteristic data and thresholds associated with stroke events and non-stroke events. In some embodiments of the invention, the baseline behavioral model is updated over time for further personalization to a user or population. For instance, baseline behavioral model can include characteristic data corresponding to stroke onset, a healthy state, sleeping, or states mimicking some of the symptoms of stroke, such as alcohol intoxication. The integration and notification module 222 can be trained against likely false positive states. The data integration and notification module 222 can integrate data, including impairment characteristics and indications of possible impairment, from the speech analytics module 214, text analytics module 216, motion analytics module 218, and/or facial analytics module 220. The data integration and notification module 222 can compare the integrated data to the baseline model to determine if stroke onset is present. In some embodiments of the invention, the data integration and notification module 222 calculates a probability of stroke onset based upon the baseline model. In some embodiments of the invention, where the data integration and notification module 222 determines the presence of stroke onset, or a likelihood of stroke onset above a threshold probability level, the data integration and notification module 222 sends an external notification to emergency medical services and/or designated individuals, such as personal physicians, emergency contacts, or family members.

Figure 5:
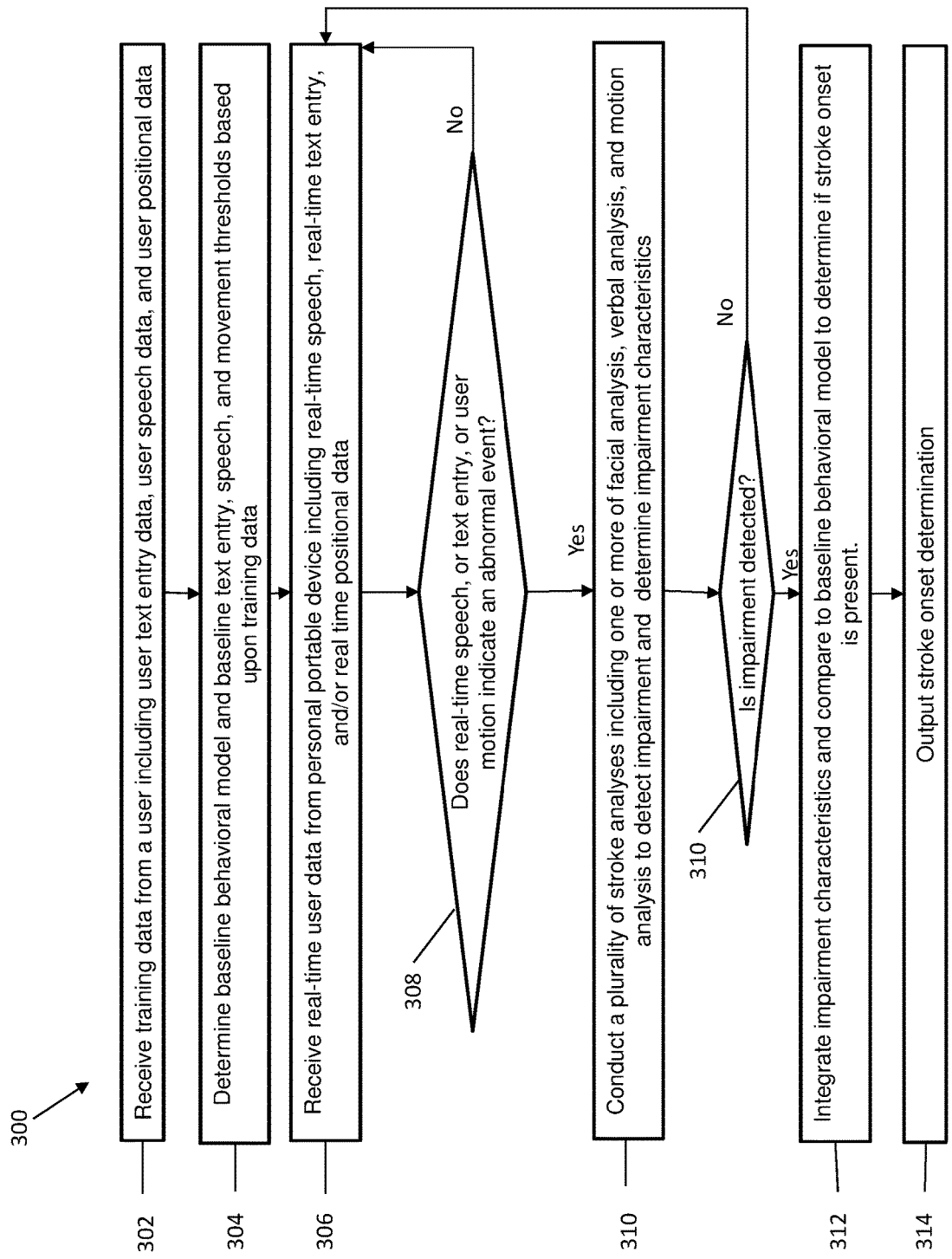
FIG. 5 is a flow diagram illustrating a method for detection and notification of stroke onset according to one or more embodiments of the present invention.

Referring now to FIG. 5, a flow chart illustrating a method 300 for detection and notification of stroke onset according to one or more embodiments of the present invention is provided. The method 300 includes, as shown at block 302, receiving training data from a user. In some embodiments of the invention, the training data includes one or more of text entry data, user speech data, and user positional data. In some embodiments of the invention, not shown, the training data includes user facial images, and generalized data for a population or for subsets of a population. The method 300 also includes, as shown at block 304, determining a baseline behavioral model and baseline text entry, speech, and movement thresholds based upon the training data. As shown at block 306, the method 300 includes receiving real-time user data including real-time speech, real time text entry, and/or real-time positional data. Next, the method 300 asks, as shown at block 308, whether the real-time speech, text entry, or user motion indicates an abnormal event. Based at least in part on a determination that the real-time speech, text entry, or user motion does not indicate an abnormal event, the method 300 returns to block 306. Based at least in part on a determination that the real-time speech, text entry, or user motion indicates an abnormal event, the method 300 proceeds to block 310, where the method 300 conducts a stroke analysis, including one or more of a facial analysis, verbal analysis, and motion analysis. In some embodiments of the invention, the stroke analysis detects impairment, including stroke impairment. In some embodiments of the invention the stroke analysis provides characteristics associated with stroke impairment indicators. Next, as shown at block 310, the method 300 asks whether impairment is detected. For example, the method 300 can determine whether impairment is detected based upon the stroke analysis results. Based at least in part on a determination that impairment is not detected, the method 300 returns to block 306. Based at least in part on a determination that impairment is detected, the method 300 proceeds to block 312 and integrates impairment characteristics and compares the integrated impairment characteristics to a baseline behavioral model to determine if stroke onset is present. The method 300 includes, as shown at block 314, outputting the stroke onset determination. For example, the output of stroke onset determination can be output locally, for example to a user, or externally, such as to emergency medical personnel.

Optionally, in some embodiments, a baseline behavioral model is personalized to the user. Such optional personalization can further improve the accuracy of stroke onset identification.

In preferred embodiments, real-time user data can include real-time speech data. In such embodiments, analyzing real-time user data can include analyzing the real-time speech data for comprehensibility and comparing the comprehensibility to a baseline comprehensibility. Inclusion of real-time speech data can, for example, facilitate detection of stroke onset when a user is communicating with or through a personal smart phone.

Optionally, real-time user data can include real-time text entry data. In such embodiments, analyzing real-time user data can include calculating a personal text input profile for the user, comparing the real-time text entry data to the personal text input profile for the user, and determining the presence of a significant text entry deviation based upon the comparison. Such embodiments can desirably increase the likelihood of stroke onset determination, for example, by enabling stroke onset detection while a user is providing text entry to a smart phone.

Optionally, real-time user data can include real-time positional data. In such embodiments, analyzing real-time user data can include calculating a personalized baseline movement model for the user, determining a plurality of real-time walking characteristics of the user, comparing the real-time walking characteristics of the user to the personalized baseline movement model for the user, and determining the presence of the abnormal event based upon the comparison. Such embodiments can desirably increase the likelihood of stroke onset determination, for example, by enabling stroke onset detection while a user is moving, including even where a user is not speaking or providing text input to a smart device.

Figure 6:
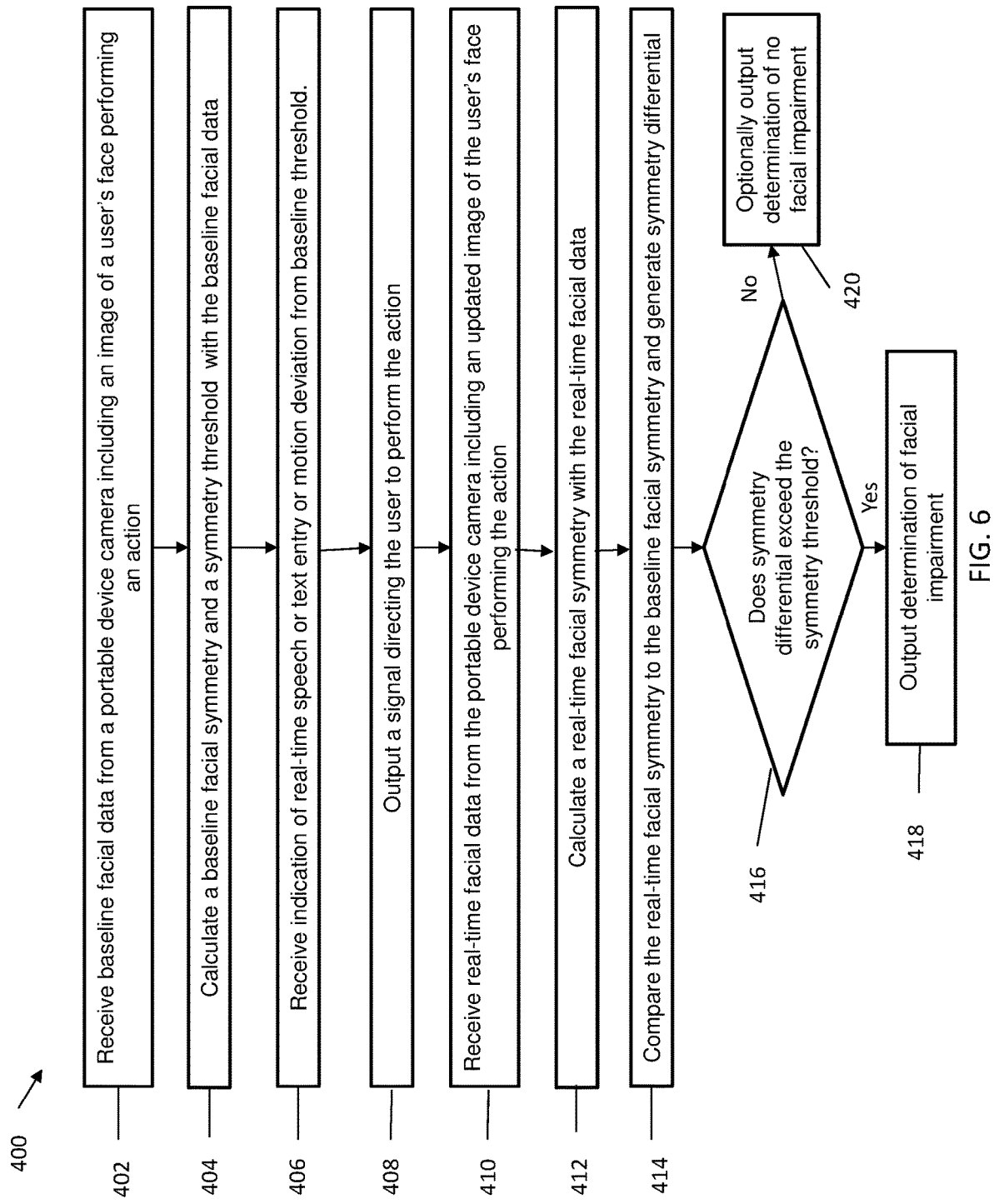
FIG. 6 is a flow diagram illustrating a method for conducting a real-time facial analysis for detection of stroke onset according to one or more embodiments of the present invention.

FIG. 6 is a flow diagram illustrating a method 400 for conducting a real-time facial analysis for detection of stroke onset according to one or more embodiments of the present invention. The method 400 includes, as shown at block 402, receiving baseline facial data from a portable device camera including an image of a user's face performing an action. The method 400 also includes, as shown at block 404, calculating a baseline facial symmetry and a symmetry threshold with the baseline facial data. The method 400 also includes, as shown at block 406, receiving an indication of real-time speech or text entry or user motion deviation from a baseline threshold. As shown at block 408, the method also includes outputting a signal directing the user to perform an action, such as a smile, a frown, or an act of performing other facial expressions. As shown at block 410, the method also includes receiving real time facial data from the portable device camera, wherein the real-time facial data includes an updated image of the user's face performing the action. In some embodiments of the invention, the method includes directing the user to perform a plurality of actions and receives real-time facial data including a plurality of update images. As shown at block 412, the method 400 includes calculating a real-time facial symmetry with the real-time facial data. As shown at block 414, the method 400 also includes comparing the real-time facial symmetry to the baseline facial symmetry and generating a symmetry differential. The symmetry differential can reflect the difference between the baseline facial symmetry and the real-time facial symmetry. Next, as shown at decision block 416, the method 400 asks whether the symmetry differential exceeds the symmetry threshold. The symmetry threshold can represent a level of facial symmetry, beyond which a user is likely to be experiencing drooping features associated with stroke. Based at least in part on a determination that the symmetry differential exceeds the symmetry threshold, the method 400 proceeds to block 418, and outputs a determination of facial impairment. Based at least in part on a determination that facial symmetry does not exceed the symmetry threshold, the method 400 optionally proceeds to block 402 and outputs a determination of no facial impairment.

Figure 7:
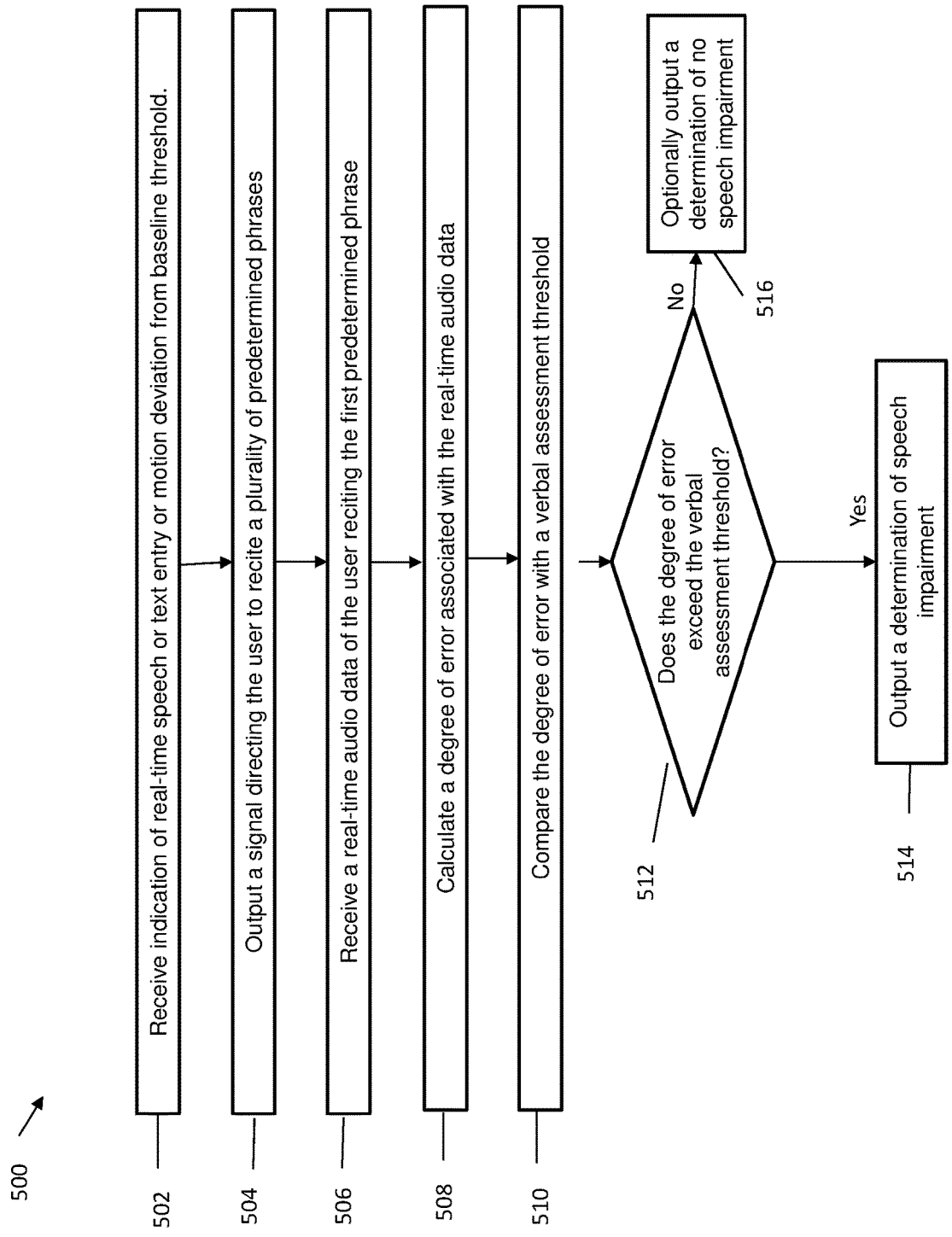
FIG. 7 is a flow diagram illustrating a method for conducting a real-time verbal analysis for detection of stroke onset according to one or more embodiments of the present invention.

FIG. 7 is a flow diagram illustrating a method 500 for conducting a real-time verbal analysis for detection of stroke onset according to one or more embodiments of the present invention. The method 500 includes, as shown at block 502, receiving an indication of real-time speech or text entry or motion deviation from a baseline threshold. The method 500 also includes, as shown at block 504, outputting a signal directing the user to recite a plurality of predetermined phrases. The predetermined phrases can be phrases known or likely to be difficult to recite when an individual is experiencing stroke onset, such as "the sky is blue." The method 500 also includes, as shown at block 506, receiving a real-time audio data of the user reciting the first predetermined phrase. The audio data can be collected, for example, by a smart phone microphone or an audio recording device in communication with a personal portable device. The method 500 also includes, as shown at block 508, calculating a degree of error associated with the real-time audio data. The degree of error can vary depending upon the complexity of the sentence. For example, in the case of the phrase "the sky is blue" a degree of error can be represented as a degree of difference between the requested phrase and received phrase or can be represented as a value of "correct" or "incorrect." The method 500 also includes, as shown at block 510 comparing the degree of error with a verbal assessment threshold. The verbal assessment threshold reflects the limit of deviation from the requested phrase, above which a user is likely to be experiencing stroke onset. The method 500 also includes, as shown at decision block 512, asking whether the degree of error exceeds the verbal assessment threshold. Based at least in part on a determination that the degree of error exceeds the verbal assessment threshold, the method 500 proceeds to block 514 and outputs a determination of speech impairment. Based at least in part on a determination that the degree of error does not exceed the verbal assessment threshold, the method 500 proceeds to block 516 and optionally outputs a determination of no speech impairment. In some embodiments of the invention, a plurality of phrases are requested and analyzed. In some embodiments of the invention, an assessment is complete after an analysis of a single phrase. Where a plurality of phrases are requested and analyzed, the degree of error for each of the phrases can be individually compared against the verbal assessment threshold or can be integrated before comparison against the verbal assessment threshold.

Figure 8:
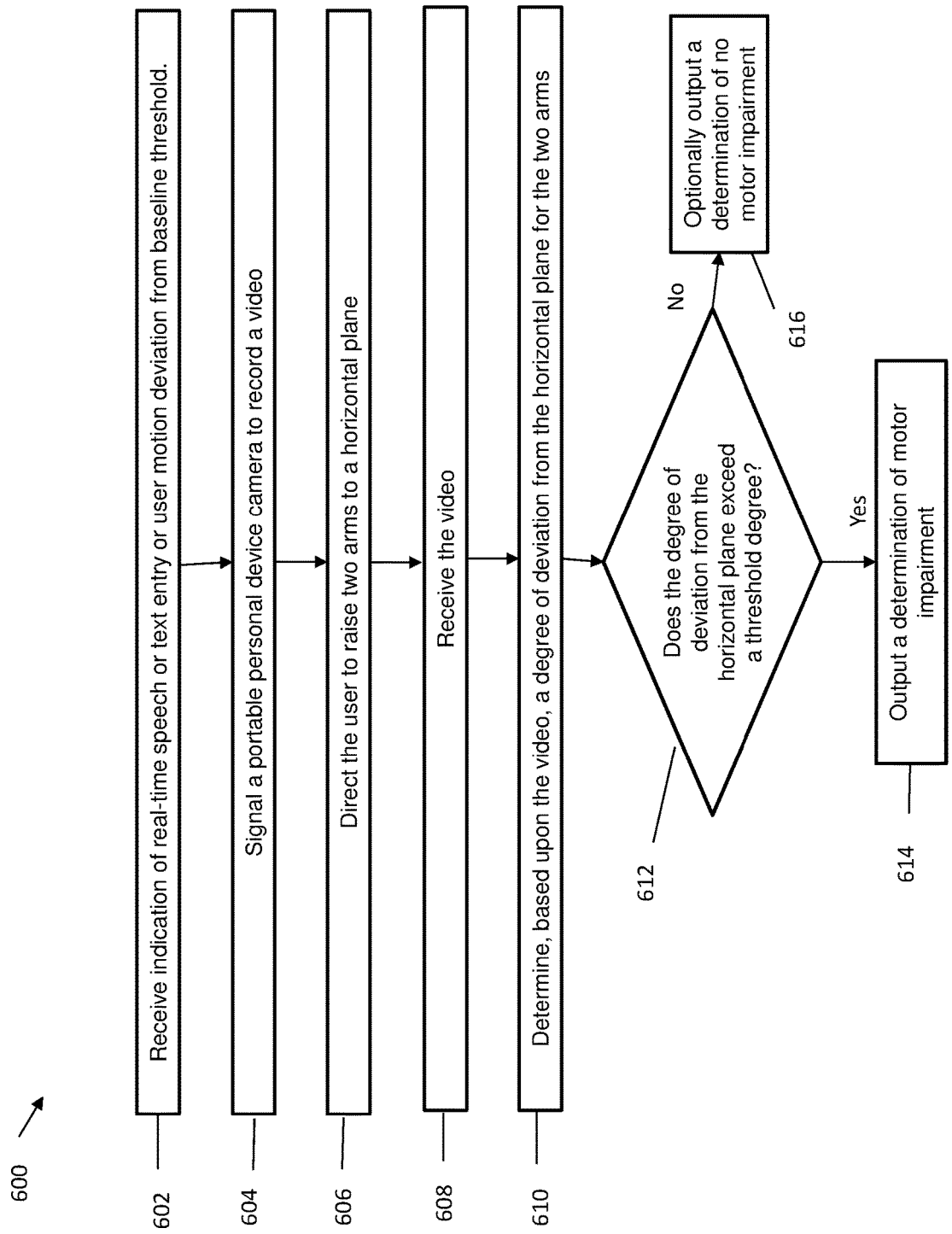
FIG. 8 is a flow diagram illustrating a method for conducting a real-time motion analysis for detection of stroke onset according to one or more embodiments of the present invention.

FIG. 8 is a flow diagram illustrating a method 600 for conducting a real-time motion analysis for detection of stroke onset according to one or more embodiments of the present invention. The method 600 includes, as shown at block 602, receiving an indication of real-time speech or text entry or motion deviation from a baseline threshold. The method 600 also includes, as shown at block 604, signaling a portable personal device camera to record a video. The method 600 also includes, as shown at block 606, directing a user to raise two arms to a horizontal plane. In some embodiment, the user is directed to raise the two arms simultaneously. In some embodiments of the invention, the user is directed to raise the two arms sequentially. The method 600 also includes, as shown at block 608, receiving the recorded video. The method 600 also includes, as shown at block 610 determining, based upon the video, a degree of deviation from the horizontal plane for the two arms. The method 600 also includes, as shown at decision block 612, asking whether the degree of deviation from the horizontal plane exceeds a threshold degree. A threshold degree is a range of degrees above and below the horizontal plane, beyond which a user is likely to be experiencing stroke onset. Based at least in part on a determination that the degree of deviation exceeds the threshold, the method 600 proceeds to block 614 and outputs a determination of motor impairment. Based at least in part on a determination that the degree of deviation does not exceed the threshold, the method 600 proceeds to block 616 and optionally outputs a determination of no motor impairment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The present invention can be a system, a method, and/or a computer program product. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer program product for determining stroke onset, the computer program product comprising:
    a computer readable storage medium readable by a processing circuit and storing program instructions for execution by the processing circuit for performing a method comprising:
    receiving training data from a user, the training data comprising text entry data;
    training a baseline behavioral model on the training data, wherein the baseline behavior model is further trained against false positive states using additional data corresponding to one or more states that mimic one or more symptoms of stroke;
    determining a baseline text entry threshold based on the baseline behavioral model;
    receiving real-time user data from a personal portable device, the real-time user data comprising real-time text entry data, the real-time text entry data comprising a text correction rate;
    analyzing the real-time user data and the baseline text entry threshold to determine the presence of an abnormal event;
    conducting a plurality of stroke analyses to generate a plurality of impairment characteristics based at least in part on a determination that the abnormal event is present;
    integrating the plurality of impairment characteristics;
    comparing the integrated plurality of impairment characteristics to the baseline behavioral model; and
    outputting a stroke onset determination.

2. The computer program product according to claim 1, wherein the baseline behavioral model is personalized to the user.

3. The computer program product according to claim 1, wherein the real-time user data comprises real-time speech data.

4. The computer program product according to claim 3, wherein analyzing the real-time user data to determine the presence of the abnormal event comprises:
    analyzing the real-time speech data for comprehensibility, and
    comparing the comprehensibility to a baseline comprehensibility.

5. The computer program product according to claim 1, wherein analyzing the real-time user data to determine the presence of the abnormal event comprises:
    calculating a personal text input profile for the user;
    comparing the real-time text entry data to the personal text input profile for the user; and
    determining the presence of a significant text entry deviation based upon the comparison.

6. The computer program product according to claim 1, wherein the real-time data comprises real-time positional data.

7. The computer program product according to claim 6, wherein analyzing the real-time user data to determine the presence of the abnormal event comprises:
    calculating a personalized baseline movement model for the user;
    determining a plurality of real-time walking characteristics of the user;
    comparing the plurality of real-time walking characteristics of the user to the personalized baseline movement model for the user; and
    determining the presence of the abnormal event based upon the comparison.

8. The computer program product according to claim 1, wherein the method further comprises conducting a facial analysis.

9. The computer program product according to claim 8, wherein the facial analysis comprises:
    receiving baseline facial data from the personal portable device, wherein the personal portable device comprises a camera, and wherein the baseline facial data comprises an image of a face the user performing an action;
    calculating a baseline facial symmetry and a symmetry threshold based upon the baseline facial data;
    outputting a signal directing the user to perform the action;
    receiving real-time facial data from the camera, wherein the real-time facial data comprises an updated user facial image;

calculate a real-time facial symmetry based upon the real-time facial data; and compare the real-time facial symmetry to the baseline facial symmetry threshold.

10. The computer program product according to claim 1, wherein the method further comprises conducting a real-time textual analysis.

11. The computer program product according to claim 1, wherein the method further comprises conducting a real-time verbal analysis.

12. The computer program product according to claim 1, wherein the method further comprises conducting a real-time motion analysis.

13. The computer program product according to claim 12, wherein the method further comprises conducting a facial analysis and a real-time verbal analysis.

14. The computer program product according to claim 1, wherein software is provided as a service in a cloud environment.

15. The computer program product according to claim 1, wherein the method further comprises sending a notification to an emergency responder.

16. A computer-implemented method for determining stroke onset, the method comprising:

receiving training data from a user, the training data comprising text entry data;

training, by a processor, a baseline behavioral model on the training data, wherein the baseline behavior model is further trained against false positive states using additional data corresponding to one or more states that mimic one or more symptoms of stroke;

determining a baseline text entry threshold based on the baseline behavioral model;

receiving, to the processor, real-time user data from a personal portable device, the real-time user data comprising real-time text entry data, the real-time text entry data comprising a text correction rate;

analyzing, by the processor, the real-time user data and the baseline text entry threshold to determine the presence of an abnormal event;

conducting, by the processor, a plurality of stroke analyses to generate a plurality of impairment characteristics based at least in part on a determination that the abnormal event is present;

integrating, by the processor, the plurality of impairment characteristics;

comparing, by the processor, the integrated plurality of impairment characteristics to the baseline behavioral model; and outputting a stroke onset determination.

17. The computer-implemented method of claim 16, wherein the baseline behavioral model is personalized to the user.

18. A processing system for determining stroke onset, comprising:

a processor in communication with one or more types of memory, the processor configured to:

receive training data from a user, the training data comprising text entry data;

train a baseline behavioral model on the training data, wherein the baseline behavior model is further trained against false positive states using additional data corresponding to one or more states that mimic one or more symptoms of stroke;

determine a baseline text entry threshold based on the baseline behavioral model;

receive real-time user data from a personal portable device, the real-time user data comprising real-time text entry data, the real-time text entry data comprising a text correction rate;

analyze the real-time user data and the baseline text entry threshold to determine the presence of an abnormal event;

conduct a plurality of stroke analyses to generate a plurality of impairment characteristics based at least in part on a determination that the abnormal event is present;

integrate the plurality of impairment characteristics;

compare the integrated plurality of impairment characteristics to the baseline behavioral model; and output a stroke onset determination.

19. The processing system of claim 18, wherein the baseline behavioral model is personalized to the user.

* * * * *